United States Patent
Shikii et al.

(10) Patent No.: US 7,724,383 B2
(45) Date of Patent: May 25, 2010

(54) IMAGE FORMATION APPARATUS

(75) Inventors: Shinichi Shikii, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1072 days.

(21) Appl. No.: 11/405,416

(22) Filed: Apr. 18, 2006

(65) Prior Publication Data
US 2006/0257040 A1 Nov. 16, 2006

(30) Foreign Application Priority Data
Apr. 18, 2005 (JP) .......................... P.2005-119622

(51) Int. Cl.
*G06F 15/00* (2006.01)
*B41J 2/00* (2006.01)

(52) U.S. Cl. ........................ 358/1.1; 347/188

(58) Field of Classification Search .................. 358/1.1, 358/1.9, 1.2, 400, 300, 1.15, 1.16, 1.13, 452, 358/453, 518; 348/207.2, 207.99, 374; 347/188, 347/189, 247; 235/462.04, 462.25; 382/167, 382/294, 128; 430/108.2, 108.9
See application file for complete search history.

(56) References Cited

U.S. PATENT DOCUMENTS
7,095,515 B2 * 8/2006 Iwadate ..................... 358/1.14

FOREIGN PATENT DOCUMENTS
JP 2004-138786 A 5/2004

* cited by examiner

*Primary Examiner*—Saeid Ebrahimi Dehkordy
(74) *Attorney, Agent, or Firm*—Sughrue Mion, PLLC

(57) ABSTRACT

An image formation apparatus comprises: an image exposure portion that forms a latent image by optically exposing a recording medium based on entered image data; a thermal development portion that visualizes the latent image by heating the recording medium exposed by the image exposure portion; at least one counter each of which counts the number of a set of the image data whenever the image data is entered; and a data-processing portion that: rotates, through 180°, (i) images represented by those of the set of the image data with the counted number of even or (ii) images represented by those of the set of the image data with the counted number of odd; and then outputs the image data to the image exposure portion.

5 Claims, 11 Drawing Sheets

IMAGE FORMATION APPARATUS

BACKGROUND OF THE INVENTION

1. Field of the Invention

The present invention relates to an image formation apparatus and, more particularly, to an image formation apparatus which is connected with plural modalities and forms images based on image data output from the modalities.

2. Description of the Related Art

In recent years, large-scale imaging diagnostic systems including radiological imaging systems (such as MRI equipment and CT scanners) and image formation apparatus (thermal development apparatus) interconnected via a network have spread widely. Data about images taken by a radiological imaging system are supplied to an image formation apparatus installed in a different room and visualized images are output.

One imaging method used in such imaging diagnostic systems is mammography. In examination of breast cancers, mammographic images of left and right breasts which have been taken mammographically and formed on a thermally developed photosensitive material are arrayed side by side and compared. The mammographic images have been visualized by imaging the breasts by a mammography imaging unit, sending data about the derived images to an image formation apparatus, optically exposing the images, and thermally developing them. In the mammography imaging unit, image data are generally treated as follows to facilitate doctor's diagnosis. One of the left and right breast images is rotated through 180° such that the left and right breast images are placed in a back to back relation about the chest walls. Then, the image data are output.

The related-art image output processing apparatus for forming mammographic images lies in a known technique consisting of forming breast images on a thermally developed photosensitive material, placing the images such that they do not touch the front or rear end of the photosensitive material in the direction of transportation or placing the images of the left and right breasts in a back to back relation about the chest wall portions, and outputting the images with optimum layout (see, for example, JP-A-2004-138786)

With this image output processing apparatus, when the thermally developed photosensitive material, which has been optically exposed and has a latent image formed thereon, is brought into contact with the heat application portion of the thermal development portion and developed, the images of the breasts are so placed that they are not formed at the front end or rear end of the thermally developed photosensitive material in the direction of transportation; otherwise, the transfer of heat from the heat application portion would become unstable, tending to cause a decrease of the concentration of the mammographic images or nonuniformity of the concentration. In this way, the effects of the concentration nonuniformity on the diagnosis are suppressed.

As described previously, the image output processing apparatus of JP-A-2004-138786 suppresses decrease and nonuniformity of the concentration of mammographic images in the direction of transportation of the thermally developed photosensitive material. However, decrease and nonuniformity of the concentration also take place in the widthwise direction perpendicular to the direction of transportation of the thermally developed photosensitive material.

In particular, each mammographic image formed on the thermally developed photosensitive material is visualized by bringing the photosensitive material into contact with the heating portion of the thermal development portion. The photosensitive material has been optically exposed by the image exposure portion and a latent image has been formed on the photosensitive material. Thus, a visible image is formed. Considerations are given to the temperature distribution of the heating portion such that the thermally developed photosensitive material is uniform in temperature in order to heat every portion of the photosensitive material with uniform temperature. However, as shown in FIG. 10A, a larger amount of heat is dissipated from each end of the heating portion than from the center. The temperature at each end tends to drop.

When a thermally developed photosensitive material is brought into contact with the heating portion having a temperature distribution in the widthwise direction as described above and development is done, there is the danger that the concentration becomes nonuniform across the width of the thermally developed photosensitive material. That is, as shown in FIGS. 10B and 10C, where the images to be developed are mammographic images which are arranged in a back to back relation about the chest wall portions like images output from a general mammography imaging unit, if an image A of the right breast and an image B of the left breast are output separately, then a mammographic image 11 to be developed which is obtained from the image A by making contact with the center of the heating portion (i.e., the heating portion of uniform temperature) is developed with desired temperature. As a result, normal concentration is obtained. On the other hand, a mammographic image 13 which is to be developed is obtained from the image B by making contact with ends of the heating portion which tend to drop in temperature is developed with lower temperature. Consequently, there is the possibility that normal concentration is not obtained.

More particularly, each point, for example, on a line a constituting the breast image A of the mammographic image 11 is brought into contact with the heating portion of given temperature $T_a$ and developed. Meanwhile, each point on a line b on the breast image B that is in a position corresponding to the line a of the breast image A is brought into contact with the heating portion of lower temperature $T_b$ and developed. Accordingly, there is the danger that comparison of corresponding portions of the breast images A and B (e.g., points $P_R$ and $P_L$) in terms of concentration and hue reveals that these portions are different in concentration and hue. Since alphanumeric information is formed in ancillary relationship to the mammographic images 11 and 13, the up-down direction of the mammographic images 11 and 13 can be discerned during outputting. In this example, for the sake of convenience, arrows are attached to the mammographic images 11 and 13, and the direction indicated by the arrows is defined as the upward direction in the figure.

The mammographic images 11 and 13 obtained in this way are arranged such that the chest wall portions $A_K$ and $B_K$ of the breast images A and B are placed in a back to back relation as shown in FIG. 11. Then, the images are placed on a showcase. The doctor observes the images A and B of the left and right breasts (mammographic images 11 and 13), discerns subtle differences in geometry and concentration between both breasts, and makes a diagnosis. However, as described previously, the corresponding portions of the breast images A and B are brought into contact with heating portions of different temperatures and developed. Consequently, they may differ in concentration and hue. There is the possibility that it is less easy for the doctor to make a diagnosis.

Accordingly, there is a demand for further improvement to prevent nonuniformity of concentration and hue in the widthwise direction perpendicular to the direction of transportation of a thermally developed photosensitive material, in addition to the direction of transportation, in order to obtain mammographic images of good quality (i.e., uniform in concentration and hue over the whole surface of each mammographic image). Furthermore, in an imaging diagnostic system having plural modalities connected with a single image formation apparatus by a network, it is essential to process mammographic image data such that image data other than mammographic images are not affected.

SUMMARY OF THE INVENTION

The present invention has been made in view of the foregoing circumstances. It is an object of the invention to provide an image formation apparatus capable of forming good-quality mammographic images which are prevented from becoming nonuniform in concentration and hue by developing images of the left and right breasts of the same patient under the same temperature conditions without affecting images other than mammographic images when images are output from the image formation apparatus connected with plural modalities.

The above-described object of the present invention can be achieved by the configurations described below.

(1) An image formation apparatus comprising: an image exposure portion that forms a latent image by optically exposing a recording medium based on entered image data; a thermal development portion that visualizes the latent image by heating the recording medium exposed by the image exposure portion; at least one counter each of which counts the number of a set of the image data whenever the image data is entered; and a data-processing portion that: rotates, through 180°, (i) images represented by those of the set of the image data with the counted number of even or (ii) images represented by those of the set of the image data with the counted number of odd; and then outputs the image data to the image exposure portion.

The image formation apparatus constructed in this way is equipped with the counter(s) for counting the number of set of image data whenever image data is entered. In forming an image, processing is performed to rotate the image through 180° for image data which results in an odd- or even-numbered total count. Therefore, when images of the left and right breasts are formed on a recording medium, portions of the images of the left and right breasts which correspond to each other are brought into contact with the same part of the heating portion and developed. Accordingly, it is assured that the portions of the images of the left and right breasts which correspond to each other are developed under the same temperature conditions. This prevents the corresponding parts of the images of the left and right breasts from becoming nonuniform in concentration and hue in spite of widthwise temperature distribution of the heating portion. In consequence, good-quality mammographic images adapted for comparative diagnosis are obtained.

(2) An image formation apparatus as set forth in (1), wherein the apparatus is connected with a plurality of modalities by a network and receives the image data sent from the modalities.

Since the image formation apparatus constructed in this way is connected with the plural modalities, images from the modalities can be output from the single image formation apparatus. Hence, the image formation apparatus can be used efficiently.

(3) An image formation apparatus as set forth in (2) above, wherein said at least one counter comprises a plurality of counters corresponding to said plurality of modalities, each of the counters counts the number of the set of image data in each of the modalities.

In the image formation apparatus constructed in this way, the counters are mounted respectively for the individual modalities. Therefore, sets of image data acquired by the individual modalities can be counted separately. This permits one of images of left and right breasts sent from the mammography imaging unit to be rotated through 180°. Good-quality mammographic images of left and right breasts whose corresponding parts do not suffer from nonuniformity in concentration and hue due to a temperature distribution across the width of the heating portion can be obtained.

(4) An image formation apparatus as set forth in (3) above, wherein when output of the image data from each of the modalities to the image formation apparatus ceases for more than a given time, each of the counters resets its counted number corresponding to each of the modalities and restart to count the number of a set of the image data.

In the image formation apparatus constructed in this way, if the output from the modalities ceases for a more than a given time, the total counts of the counters mounted for the modalities are reset. Sets of the image data are restarted to be counted. Therefore, with respect to sets of image data which correspond to individual images and are independently output at intervals of time, images are created without performing processing for rotating the images.

(5) An image formation apparatus as set forth in any one of (1)-(4) above, wherein the set of the image data comprises a pair of image data in which one is about a left breast and the other one is about a right breast, and the data-processing portion performs image processing to rotate any one of said pair of image data in such a way that each of chest wall portions under the left and right breasts in images to be formed on the recording medium based on said pair of image data extends along an end portion of the recording medium that are parallel to a direction of transportation of the recording medium and that the images of the left and right breasts are oriented in the same direction.

In the image formation apparatus constructed in this way, the chest wall portions of the images of the left and right breasts of the same patient are formed along the end portions extending parallel to the direction of transportation of the recording medium and that the images of the left and right breasts are oriented in the same direction. Therefore, the parts of the images of the left and right breasts which correspond to each other can be developed under the same temperature conditions. Consequently, mammographic images of the left and right breasts which are not nonuniform in concentration and hue can be obtained.

DETAILED DESCRIPTION OF THE INVENTION

Figure 1:
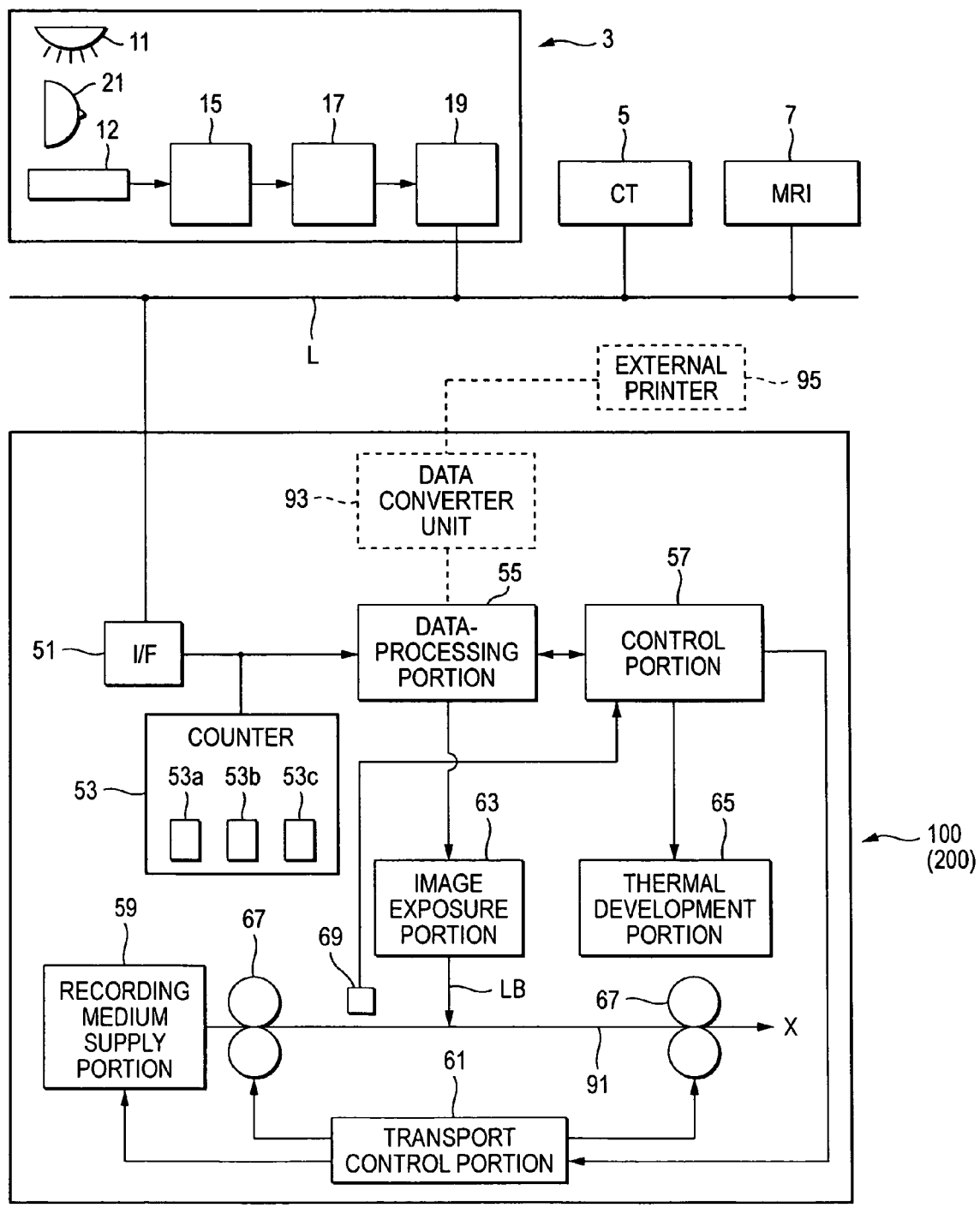
FIG. 1 is a block diagram of an image formation apparatus connected with plural modalities including a mammography imaging unit.
Figure 2:
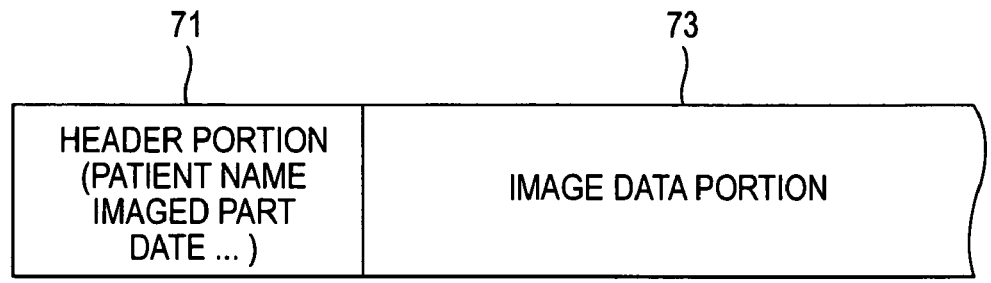
FIG. 2 is a diagram illustrating the structure of data obtained by the modalities including the mammography imaging unit.

Preferred embodiments of an image formation apparatus associated with the present invention are hereinafter described in detail with reference to the drawings. FIG. 1 is a block diagram of an image formation apparatus connected with a plurality of modalities including a mammography imaging unit. FIG. 2 is a diagram illustrating the structure of data obtained from each modality including the mammography imaging unit.

As shown in FIG. 1, an image formation apparatus 100 of the present invention is connected with a mammography imaging unit 3, a CT scanner 5, and MRI equipment 7, which are modalities, by a communication line L.

The modality that presents a problem in the present invention is the mammography imaging unit 3 and so the structure of the mammography imaging unit 3 is first described. As shown in FIG. 1, the imaging unit 3 has an X-ray source 11, an X-ray capture section 12 consisting of a stimulable phosphor sheet, flat panel detector, or the like, an image data creation portion 15 for converting the image obtained from the X-ray capture section 12 into data about a breast image, an image-processing portion 17 for adding a header portion including ID information to the created breast image data or performing image processing, for example, for rotation, and a communication interface (IF) 19 that outputs the breast image data.

The structure of the data created by the mammography imaging unit 3 that includes other type of imaging unit such as MRI equipment is stipulated by the DICOM standard. As shown in FIG. 2, the data structure consists of a header portion 71 and an image data portion 73 recorded subsequently to the header portion 71. The ID information is recorded in the header portion 71. Image data (here, breast image data) is recorded in the image data portion 73. Various kinds of information (such as patient name, imaged parts, date of imaging, and imaging equipment name) ancillary to the image data are recorded as the ID information.

In the following description, the ID information in the header portion 71 and the image data in the image data portion 73 are collectively referred to simply as the acquired image data.

As shown in FIG. 1, the mammography imaging unit 3 directs X-rays at the breasts 21 of an examinee from the X-ray source 11. The transmitted radiation is captured by the X-ray capture section 12. The captured radiation is converted into breast image data by the image data creation portion 15. The image data is further subjected to given image processing by the image-processing portion 17. The obtained data is sent to the image formation apparatus 100 from the communication interface 19 via the communication line L.

Embodiments of the thermally developed recording apparatus 100 that is one example of the image formation apparatus are next described.

The thermally developed recording apparatus 100 performs scan and exposure while modulating the output light from the image exposure portion based on the input image data. In this way, a latent image is formed on the thermally developed recording material. Then, the latent image is visualized by heating the material in the thermal development portion. Image data acquired by the mammography imaging unit 3 is sent to the thermally developed recording apparatus 100 via the communication line L.

FIRST EMBODIMENT

As shown in FIG. 1, the thermally developed recording apparatus 100 forms a latent image by exposing the thermally developed recording material to a light beam consisting of laser light, using the thermally developed recording material consisting of a thermally developed photosensitive material or photosensitive and heat-sensitive recording material that is a recording medium which does not need moist development. Then, the thermally developed recording material is heated by the thermal development portion to visualize the latent image. Then, the image is cooled down to room temperature.

The thermally developed recording apparatus 100 has a communication interface (IF) 51, a counter unit 53, a data-processing portion 55, a control portion 57 for controlling various mechanisms according to a given procedure, a thermally developed recording material supply portion 59 for taking out film sheets of a thermally developed recording material 91 one by one from a cassette (not shown) or paying out a film sheet in the form of a roll to a transport section 67, a transport control portion 61 for controlling the operation of the transport section 67, an image exposure portion 63 for scanning the laser beam LB based on data about breast images in the main scan direction for exposure and forming a latent image on the thermally developed recording material 91 that is conveyed in an auxiliary scan direction (i.e., in the transport direction) substantially perpendicular to the main scan direction, and a thermal development portion 65 for elevating the temperature while transporting the thermally developed recording material 91 to visualize the latent image.

The aforementioned thermally developed photosensitive material or photosensitive and heat-sensitive recording material can be used as the thermally developed recording material 91. The thermally developed photosensitive material is a recording material that records (exposes) images by the use of a light beam (such as laser beam LB) and then produces colors by thermal development. The photosensitive and heat-sensitive recording material is a recording material that records images by means of a light beam and then produces colors by thermal development.

The counter unit 53 counts the number of sets of the acquired image data entered into the thermally developed recording apparatus 100. The counter counts the number of stored input sets of data upward whenever acquired image data is entered. The counter unit 53 is only required to discern the order of input of at least two image data sets obtained most recently out of the entered acquired image data. The counter unit is not always a so-called hardware counter that counts input data upward. For example, it may be a flag whose state of storage is inverted whenever acquired image data is entered.

Where the counter unit 53 counts the number of input data items upward whenever acquired image data is entered, the order of input of the acquired image data sets is determined according to whether the total count of the counter unit is odd or even. Where the counter unit 53 is made of a flag, the order of input of the acquired image data sets is discerned by reading out the contents of the flag.

In the following description, the counter unit 53 is made of a so-called hardware counter that counts entered data items upward.

With respect to the counter unit 53 of the thermally developed recording apparatus 100 of the first embodiment, there are plural counters for each of the connected modalities. More specifically, the counter unit includes a counter 53a for the mammography imaging unit 3, a counter 53b for the CT scanner 5, and a counter 53c for the MRI equipment 7. The counter 53a counts the number of input data items upward whenever image data acquired by the imaging unit 3 is entered from it. The counter 53b counts the number of input data items upward whenever image data acquired by the CT scanner 5 is entered. The counter 53c counts the number of input data items whenever image data acquired by the MRI equipment 7 is entered.

The data-processing portion 55 processes the image data entered from the modality in a given manner (described later) and outputs the processed data to the image exposure portion 63.

The image exposure portion 63 is a unit for exposing the thermally developed recording material 91 by light beam scanning and exposure, and has an auxiliary scan transport portion (transport section 67) such as a transport roller and a scanning-and-exposing portion (laser irradiation section). The scanning-and-exposing portion has a scanning portion including a laser light source and a polygon mirror. The scanning-and-exposing portion scans (principal scan) the laser beam LB while controlling the output of the laser in accordance with image data sent out from the data-processing portion 55. At this time, the thermally developed recording material 91 is conveyed accurately in the auxiliary scan direction by the auxiliary scan transport portion (transport section 67) whose amount of feed is controlled by the transport control portion 61.

A leading edge detection sensor 69 that is a recording medium detection section is positioned in the transport path immediately ahead of the image exposure portion 63 as viewed in the direction of transportation. The sensor 69 detects the leading edge of the thermally developed recording material 91 in the direction of transport, the recording material being conveyed along the transport path, and outputs a recording medium detection signal to the control portion 57.

The thermal development portion 65 heats and develops the thermally developed recording material 91 which has been exposed and which has a latent image thereon. For example, the thermal development portion 65 is equipped with a curved plate heater having a curved heating surface. The thermal development portion 65 is also equipped with plural holding rollers which are mounted opposite to the heating surface of the curved plate heater and press the recording medium conveyed over the heating surface against the heating surface and convey the medium. The thermally developed recording material 91 is pressed against the curved plate heater by the holding rollers and elevated in temperature. Thus, the latent image is visualized.

Figure 3:
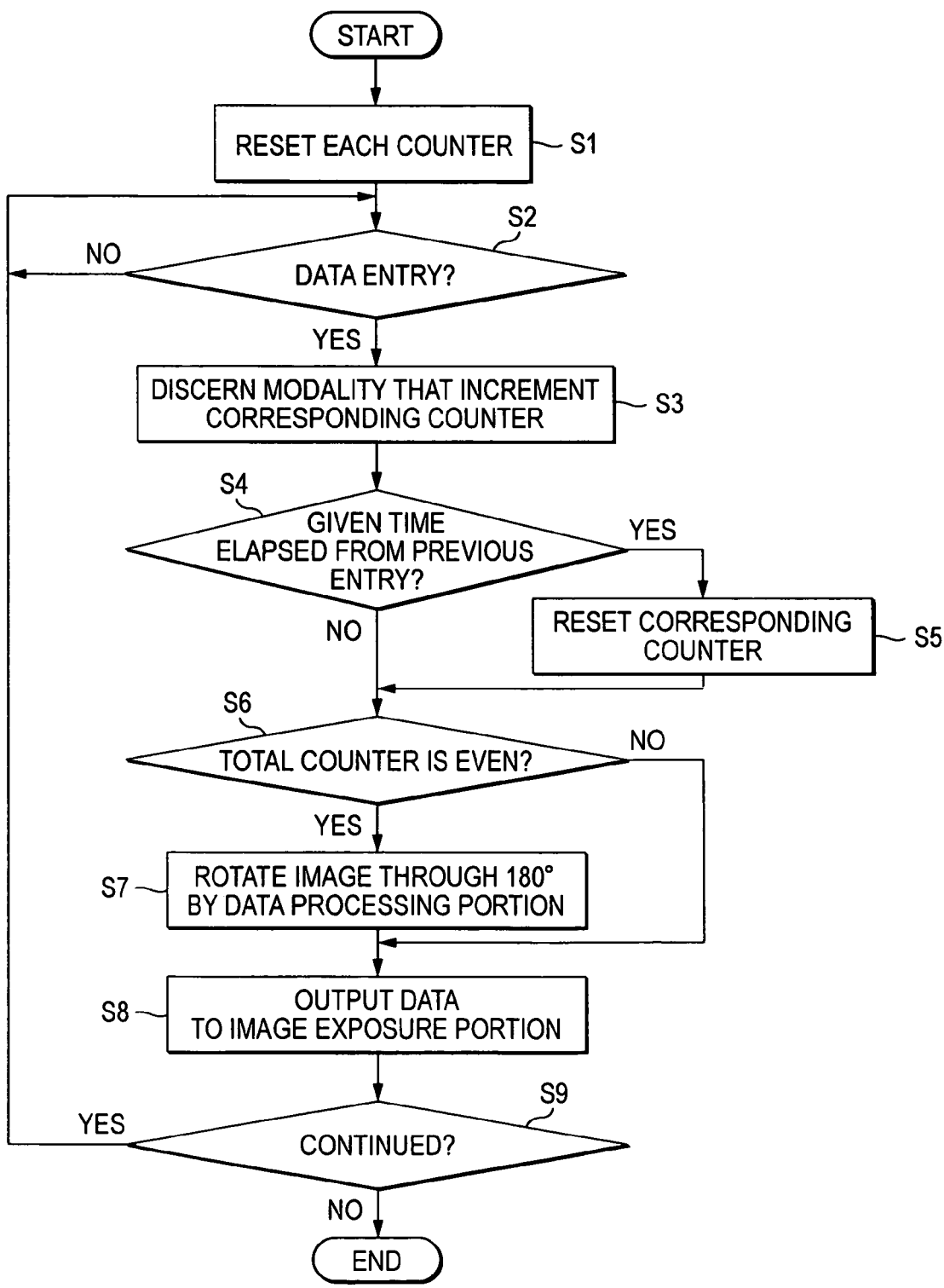
FIG. 3 is a flowchart illustrating a procedure performed by an image formation apparatus of a first embodiment to process data.

The operation of the thermally developed recording apparatus 100 constructed as described above is next described by referring to the flowchart of FIG. 3.

When operation of the thermally developed recording apparatus 100 is started, the thermally developed recording material 91 accommodated in the thermally developed recording material supply portion 59 is taken out and started to be transported in the direction of the arrow X by the transport section 67 (see FIG. 1). At the same time, the contents of the counters 53a, 53b, and 53c corresponding to the modalities are reset (S1).

A decision is made as to whether the acquired image data has been entered into the thermally developed recording apparatus 100 from the modalities (i.e., mammography imaging unit 3, CT scanner 5, and MRI equipment 7) via the communication line L and communication interface 51 (S2). If no data is entered, control returns to the first step, where the apparatus waits for entry of data. If data is entered, the modality that has sent the acquired image data is discerned from the ID information (imaging unit name) of the header portion 71 of the image data. The corresponding counter in the counter unit 53 (e.g., counter 53a in a case where the acquired image data is sent from the mammography imaging unit 3) counts up with the input data items (i.e., the counter is incremented) (S3).

Then, a decision is made as to whether a given time has elapsed from the previous entry of data to the present entry of data (S4). If the decision is affirmative (Yes), the contents of the counter in the counter unit 53 corresponding to the modality are reset (S5). If the decision is negative (No), a decision is immediately made as to whether the total count of the counter is odd or even (S6). If it is not even, i.e., odd, then the image data is intact output to the image exposure portion 63 from the data-processing portion 55 (S8). The laser beam LB is shone on the thermally developed recording material 91 based on the acquired image data to form a latent image on the material 91.

Scanning of the laser beam LB is started after a lapse of a given time since the leading edge of the conveyed, thermally developed recording material 91 as viewed in the direction of conveyance of the material 91 has been detected by the leading edge detection sensor 69. Therefore, the upper end of the image of each breast is formed in a position spaced from the leading edge of the recording material 91 as viewed in the direction of transportation by a given distance. It is unlikely that a part of the breast image is formed outside the recording material 91. Rather, the whole image fits within the recording material 91.

If the total count of the counter unit 53 is judged to be even (S6), the data-processing portion 55 performs data processing such that the image is rotated through 180° (S7). Then, the data is output to the image exposure portion 63 (S8). Based on the image data, a latent image is created.

Then, a decision is made as to whether the operation for forming an image is continued (S9). If the operation is continued, control returns to the first step, where it waits for entry of data. If the operation is not continued, the processing for forming an image is ended.

According to the processing procedure illustrated in the flowchart of FIG. 3, sets of image data from the modalities connected with the thermally developed recording apparatus 100 are processed such that every other image is rotated through 180°, and images are formed. Since every other image is simply rotated through 180° and all the images are output, the images themselves are not affected at all. In other words, this process step substantially acts only on a pair of mammographic images of the left and right breasts which are compared for diagnosis. Images from other modalities are not substantially affected.

In the flowchart illustrated in FIG. 3, data processing is performed such that only images providing even-numbered total counts are rotated through 180°. Alternatively, only images providing odd-numbered total counts may be rotated through 180°. In summary, two successive sets of mammographic image data originating from the same patient can be judged to have arisen from the left and right breasts. Either one image may be rotated through 180°, and images may be formed.

By processing the acquired image data as described above, the following advantages are produced. These are described by referring to FIGS. 4-7.

Figure 4A:
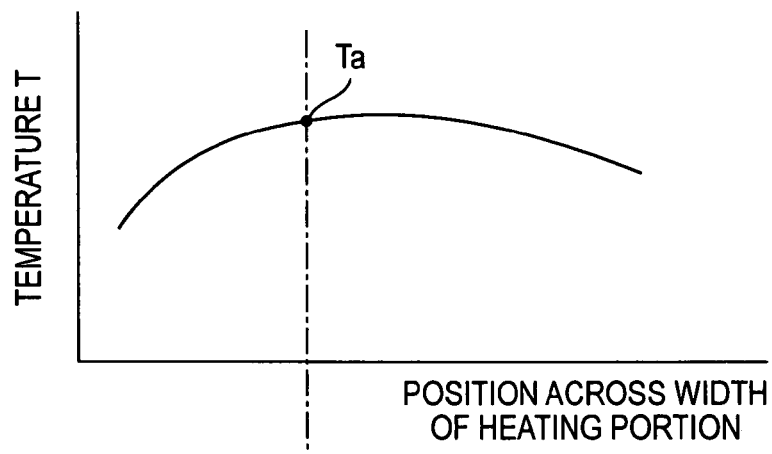
FIGS. 4A to 4C illustrate mammographic images that are thermally developed by a heating portion having a temperature distribution in its widthwise direction.
Figure 4B:
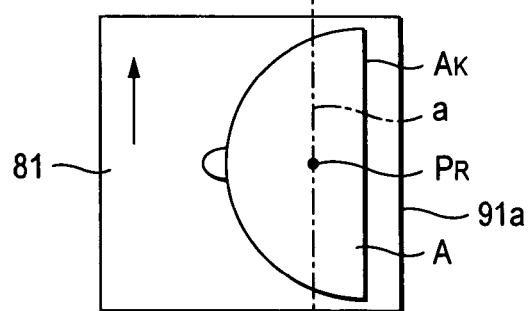
Figure 4C:
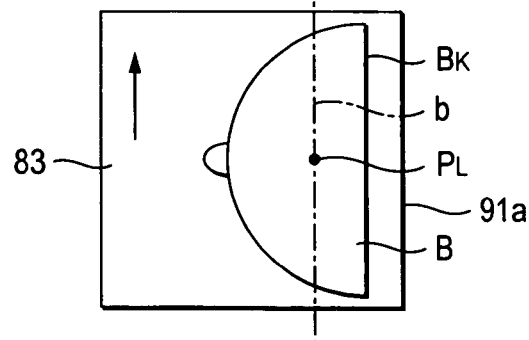

FIGS. 4A-4C illustrate the relation between the temperature distribution across the heating portion and a thermal development position on the recording medium. In FIG. 4A, the temperature of the heating portion is plotted against the widthwise position of the image. FIG. 4B shows a mammographic image including an image of one breast A out of images of the left and right breasts. FIG. 4C shows a mammographic image including an image of the other breast B.

As shown in FIGS. 4A-4C, the mammographic images 81 and 83 have been formed after rotating any one (e.g., image B of the breast) of the images of the left and right breasts through 180° by the data-processing portion 55 (see FIG. 1). The images 81 and 83 contain an image A of the right breast and the image B of the left breast, respectively. The images A and B have chest wall portions $A_K$ and $B_K$, respectively, which extend along a right-end portion 91a that is parallel to the direction of transportation of the thermally developed photosensitive material 91. Furthermore, the images A and B of the breasts are oriented in the same direction (in the leftward direction in the illustrated embodiment). This is to be compared with FIGS. 10A to 10C formed by the related art. Accordingly, the parts of the images A and B of the breasts which correspond to each other (e.g., each point on a line a extending across the breast image A and each point on a line b extending across the breast image B) are brought into contact with the same part of the heating portion of the thermal development portion 65 and developed.

In other words, each point on the lines a and b is brought into contact with the heating portion of given temperature $T_a$ and developed. Accordingly, each point on the line a on the breast image A does not differ in concentration or hue from each point on the line b on the breast image B in spite of the developing temperature. Similar principle applies to other corresponding parts of the breast images A and B. Throughout each of the obtained breast images A and B, their respective corresponding parts are stable in concentration and hue.

Figure 5:
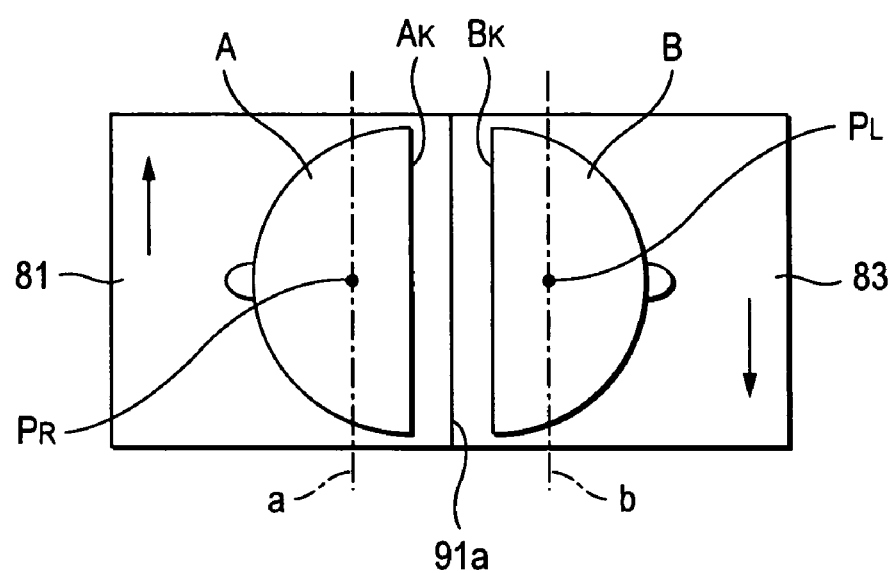
FIG. 5 shows the manner in which the left and right mammographic images of FIGS. 4B and 4C are arranged such that the chest wall portions are placed in a back to back relation and then the images are placed on a showcase.

FIG. 5 shows the state in which the left and right mammographic images obtained in FIGS. 4B and 4C have been placed such that their chest wall portions are in a back to back relation and then the images have been applied on a showcase.

With respect to the mammographic images 81 and 83 obtained in this way, the chest wall portions $A_K$ and $B_K$ of the breast images A and B are placed in a back to back relation as shown in FIG. 5. The images are then applied on a showcase. Since the corresponding parts of the left and right breast images A and B (e.g., point $P_R$ on the breast image A and point $P_L$ on the breast image B) are stable in concentration and hue. Consequently, the doctor who compares the images A and B can easily discern subtle differences in shape and concentration between the left and right breast images A and B.

Figure 6A:
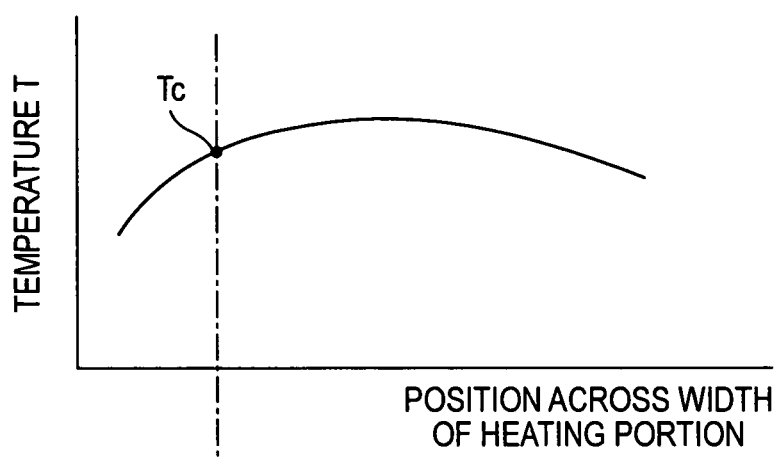
FIGS. 6A to 6C illustrate mammographic images that are thermally developed by a heating portion having a temperature distribution in its widthwise direction.
Figure 6B:
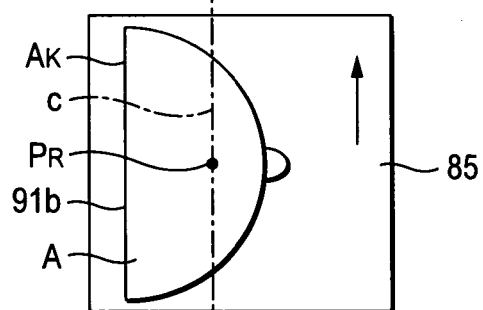
Figure 6C:
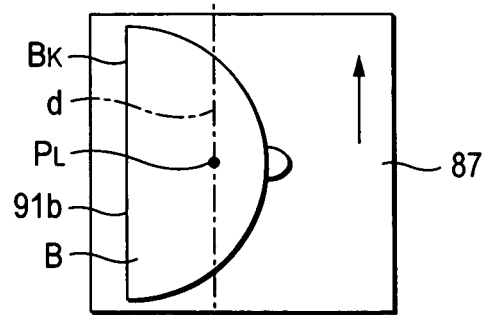

FIGS. 6A-6C illustrate the relation between the temperature distribution across the heating portion and the thermal development position on the recording medium. In FIG. 6A, temperature is plotted against the position of the heating portion across the width of the image. FIG. 6B shows a mammographic image including one breast image A of left and right breast images. FIG. 6C shows a mammographic image including the other breast image B.

Figure 10A:
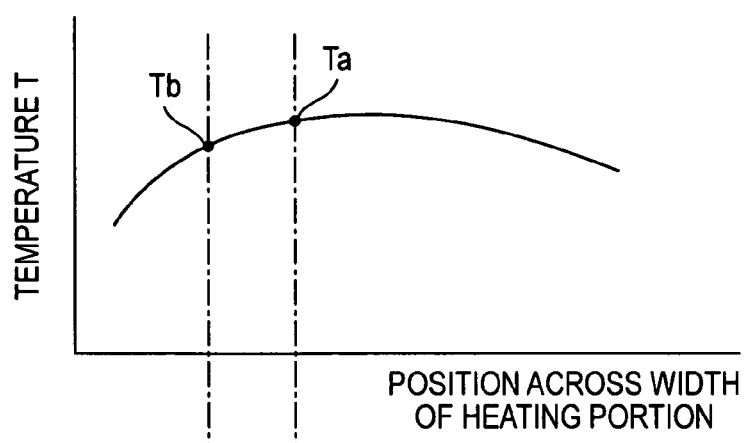
FIGS. 10A to 10C illustrate mammographic images that are thermally developed in the related art by a heating portion having a temperature distribution in its widthwise direction.
Figure 10B:
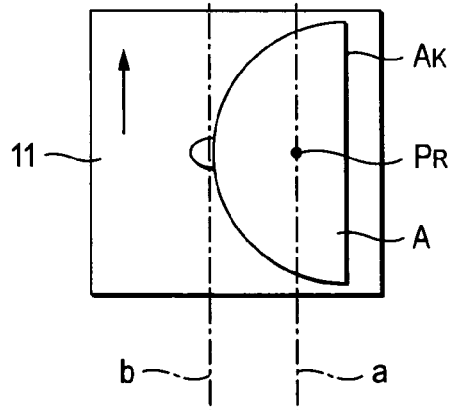
Figure 10C:
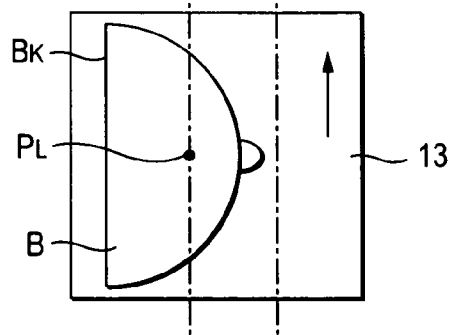
Figure 11:
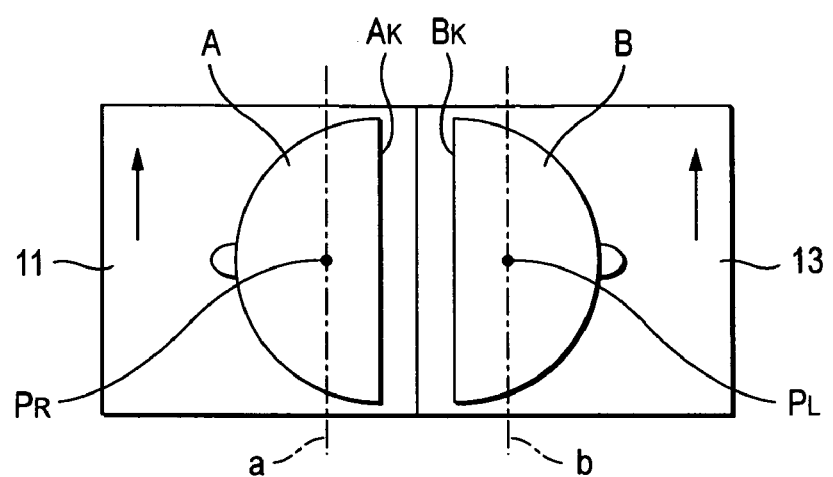
FIG. 11 shows the manner in which related-art mammographic images are arranged such that the chest wall portions are placed in a back to back relation and then the images are placed on a showcase.

As shown in FIGS. 6A-6C, mammographic images 85 and 87 contain breast images A and B, respectively. The breast image A has been rotated through 180°. The breast images A and B have chest wall portions $A_K$ and $B_K$, respectively, which extend along the left-end portions 91b that are parallel to the direction of transportation of the thermally developed photosensitive material 91. The breast images A and B are oriented in the same direction (in the rightward direction in the illustrated embodiment). This is to be compared with FIGS. 10A to 10C illustrating the related art. Parts of the breast images A and B which correspond to each other (e.g., each point on a line c on the breast image A and each point on a line d on the breast image B) are brought into contact with the same part of the heating portion of the thermal development portion 65 and developed.

Since each point on the lines c and d is brought into contact with the heating portion of temperature $T_c$ and developed, each point on the line c on the breast image A and each point on the line d on the breast image B are prevented from becoming nonuniform in concentration and hue in spite of developing temperature. Similar principle applies to other corresponding parts of the breast images A and B. The corresponding parts of the breast images A and B are stable in concentration and hue over the whole of each of the images A and B.

Figure 7:
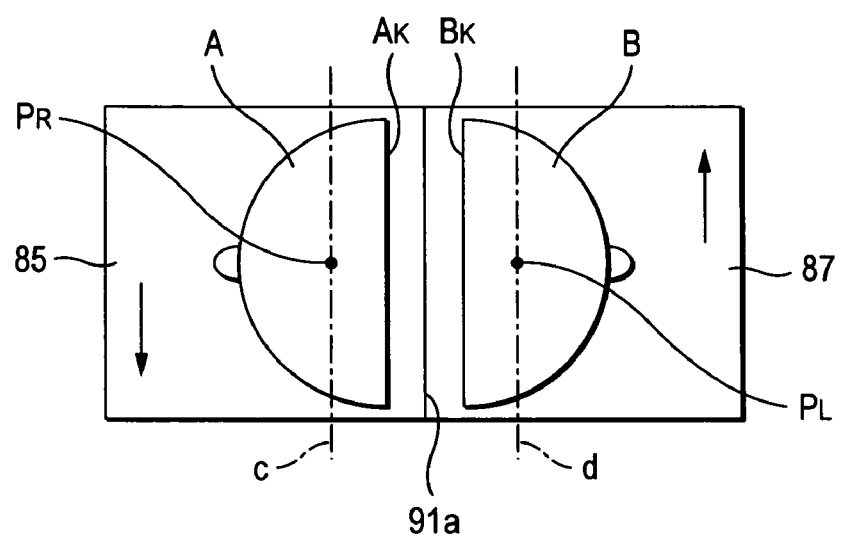
FIG. 7 shows the manner in which the left and right mammographic images of FIGS. 6B and 6C are arranged such that the chest wall portions are placed in a back to back relation and then the images are placed on a showcase.

FIG. 7 shows the state in which the left and right mammographic images obtained in FIGS. 6B and 6C have been placed such that their chest wall portions are in a back to back relation and then the images have been applied on a showcase.

With respect to the mammographic images 85 and 87 obtained in this way, the chest wall portions $A_K$ and $B_K$ of the breast walls A and B are placed in a back to back relation as shown in FIG. 7. The images are then applied on a showcase. Since the corresponding parts of the left and right breast images A and B (e.g., point $P_R$ in the breast image A and point $P_L$ in the breast image B) are stable in concentration and hue. Consequently, the doctor can easily discern subtle differences in shape and concentration between the left and right breast images A and B.

In a diagnosis conducted in a medical institution, a thermally developed recording apparatus 100 which can treat image data acquired in accordance with the DICOM standard and which outputs accurate diagnostic images is necessary. However, reference images and other images handed over to the patient for informed consent are not always necessary to be fully detail. A commercially available printer connected with a personal computer and used (e.g., an ink-jet printer) can be sufficiently used as the image formation apparatus that outputs such reference images. This is advantageous in terms of cost.

Since any commercially available printer cannot treat image data acquired in accordance with the DICOM standard, a data converter unit 93 equipped with a hard disk drive (not shown) may be mounted within the thermally developed recording apparatus 100 as indicated by the broken line in FIG. 1. The converter unit 93 converts DICOM standard-based image data received from the data-processing portion 55 into a data format that can be treated by a commercially available external printer. The converted data is output to the external printer 95, which in turn prints out reference images. In the illustrated embodiment, the data converter unit 93 is incorporated within the thermally developed recording apparatus 100. The data converter unit 93 may also be an independent unit mounted outside the recording apparatus 100 and connected with it by a communication cable. Images formed by such a simple external printer are advantageous in a case where they are used as reference images.

SECOND EMBODIMENT

A thermally developed recording apparatus 200 of a second embodiment is similar to the thermally developed recording apparatus 100 of the first embodiment except that the counter unit 53 consists of a single counter. Therefore, in the following description, FIG. 1 illustrating the thermally developed recording apparatus 100 of the first embodiment is also referenced.

The counter unit 53 of the thermally developed recording apparatus 200 of the second embodiment modifies the storage contents when data is entered from whatever modality without discriminating between the modalities (e.g., mammography imaging unit 3, CT scanner 5, and MRI equipment 7) connected with the recording apparatus 200. That is, where the counter unit 53 consists of a so-called hardware counter, it upwardly counts input data items to be stored whenever data is entered. Where the counter unit 53 is a flag, its storage state is inverted.

Figure 8:
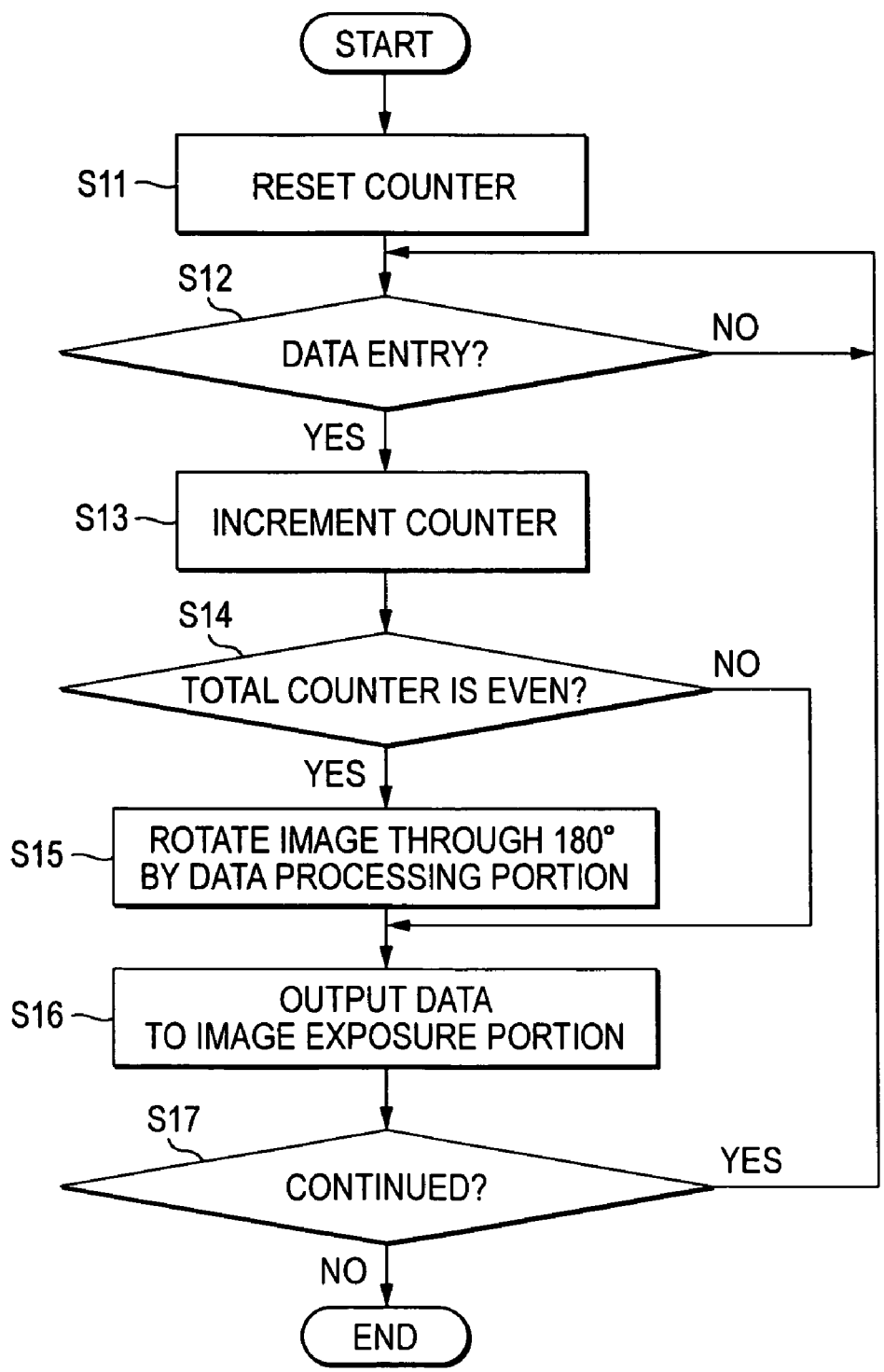
FIG. 8 is a flowchart illustrating a procedure performed by an image formation apparatus of a second embodiment to process data.

The operation of the thermally developed recording apparatus 200 of the structure described above is next described by referring to the flowchart of FIG. 8.

As shown in FIG. 1, when operation of the thermally developed recording apparatus 200 is started, the thermally developed recording material 91 accommodated in the thermally developed recording material supply portion 59 is taken out and started to be conveyed in the direction of the arrow X by the transport section 67. At the same time, as shown in FIG. 8, the contents of the counter unit 53 are reset (S11).

A decision is made as to whether the acquired image data has been entered into the thermally developed recording apparatus 200 from the modalities (mammography imaging unit 3, CT scanner 5, and MRI equipment 7) via the communication line L and communication IF 51 (S12). If no data has been entered, control returns to the first step, where the apparatus waits for entry of data. If data has been entered, the counter unit 53 counts upward (is incremented) (S13). Then, a decision is made as to whether the total count of the counter unit 53 is even or not (S14). If it is not even, i.e., odd, the image data is intact output to the image exposure portion 63 from the data-processing portion 55 (S16). Based on the acquired image data, laser beam LB is shone on the thermally developed recording material 91 to form a latent image on the material.

If the total count of the counter unit 53 is judged to be even (S14), the image data is processed by the data-processing portion 55 such that the image is rotated through 180° (S15). Then, the data is output to the image exposure portion 63 (S16). A latent image is created based on the image data. A decision is made as to whether the operation for forming an image is continued (S17). If the operation is continued, control returns to the first step, where the apparatus waits for entry of data. If the operation is not continued, the processing for forming an image is ended.

As described previously, the image processing performed by the thermally developed recording apparatus 200 simply rotates every other one of the images entered into the recording apparatus 200 from any modality irrespective of the type of the modality that sends the acquired image data to the recording apparatus 200. The acquired image data sent from the mammography imaging unit 3 always contains image data about successive pairs of breast images. Therefore, because of the processing described above, every image that gives an even or odd total count is rotated. Accordingly, this apparatus yields the same advantages as the thermally developed recording apparatus 100 of the first embodiment already described in connection with FIGS. 4-7.

Furthermore, with respect to the image data acquired from modalities other than the mammography imaging unit 3, some of the images indicated by the image data are rotated. Each such image is simply rotated through 180° and so the original image is regained if the image is rotated through 180° when applied on a showcase. Consequently, the diagnosis will not be hindered.

Figure 9:
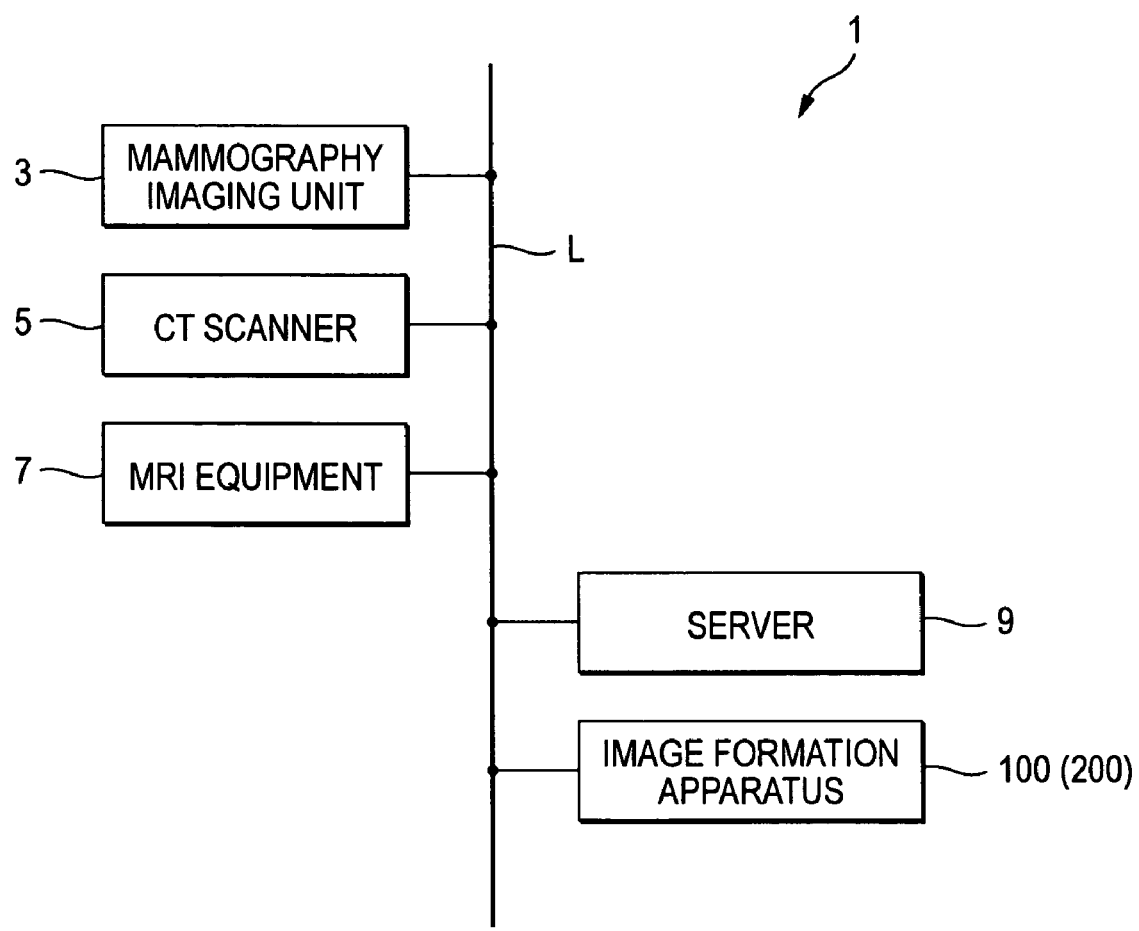
FIG. 9 is a diagram of a large-scale imaging diagnostic system including a server.

It is to be understood that the image formation apparatus associated with the present invention is not limited to the above-described embodiments but rather modifications and improvements can be made appropriately. In the present embodiment, rotation of images indicated by image data is performed by the data processing portion disposed in the data formation apparatus. The rotation may be performed anywhere as long as prior to exposure of the recording medium performed by the image exposure portion. For example, as shown in FIG. 9, in a case where a large-scale imaging diagnostic system 1 including a server 9 as its component is built, the counting means or counter unit 53 and data-processing portion 55 disposed within the image formation apparatus 100 or 200 in the above embodiments may be disposed within the server 9. Image data may also be output after performing the processing for rotating images by the server 9. This modified embodiment also yields the same advantages as the above-described embodiments.

The image formation apparatus of the present invention outputs images according to image data entered from the plural modalities. When the apparatus outputs mammographic images, the parts of the images of the left and right breasts which correspond to each other are developed under the same temperature conditions. Therefore, the corresponding parts of the images of the left and right breasts do no suffer from nonuniformity in concentration and hue due to a temperature distribution across the heating portion. Good-quality mammographic images can be formed. This facilitates making a comparative diagnosis of the images of the left and right breasts. Also, images other than the mammographic images are not affected.

The entire disclosure of each and every foreign patent application from which the benefit of foreign priority has been claimed in the present application is incorporated herein by reference, as if fully set forth.

What is claimed is:

1. An image formation apparatus comprising:
   an image exposure portion that forms a latent image by optically exposing a recording medium based on entered image data;
   a thermal development portion that visualizes the latent image by heating the recording medium exposed by the image exposure portion;
   at least one counter each of which counts the number of a set of the image data whenever the image data is entered; and
   a data-processing portion that: rotates, through 180°, (i) images represented by those of the set of the image data with the counted number of even or (ii) images represented by those of the set of the image data with the counted number of odd; and then outputs the image data to the image exposure portion.

2. An image formation apparatus as set forth in claim 1, wherein the apparatus is connected with a plurality of modalities by a network and receives the image data sent from the modalities.

3. An image formation apparatus as set forth in claim 2, wherein said at least one counter comprises a plurality of counters corresponding to said plurality of modalities, each of the counters counts the number of the set of image data in each of the modalities.

4. An image formation apparatus as set forth in claim 3, wherein when output of the image data from each of the modalities to the image formation apparatus ceases for more than a given time, each of the counters resets its counted number corresponding to each of the modalities and restart to count the number of a set of the image data.

5. An image formation apparatus as set forth in claim 1, wherein the set of the image data comprises a pair of image data in which one is about a left breast and the other one is about a right breast, and the data-processing portion performs image processing to rotate any one of said pair of image data in such a way that each of chest wall portions under the left and right breasts in images to be formed on the recording medium based on said pair of image data extends along an end portion of the recording medium that are parallel to a direction of transportation of the recording medium and that the images of the left and right breasts are oriented in the same direction.

\* \* \* \* \*